(12) United States Patent
Gray et al.

(10) Patent No.: US 8,987,545 B2
(45) Date of Patent: Mar. 24, 2015

(54) FEMININE HYGIENE ABSORBENT ARTICLES COMPRISING WATER-ABSORBING POLYMER PARTICLES

(75) Inventors: Brian Francis Gray, Cincinnati, OH (US); Achille Di Cintio, Pescara (IT); Giovanni Carlucci, Chieti (IT); Francisco Javier Lopez Villanueva, Schifferstadt (DE); Markus Linsenbuehler, Heidelberg (DE); Matthias Weismantel, Jossgrund (DE); Bernd Adolf Siegel, Otterstadt (DE)

(73) Assignee: The Procter & Gamble Company, Cincinnati, OH (US)

( * ) Notice: Subject to any disclaimer, the term of this patent is extended or adjusted under 35 U.S.C. 154(b) by 316 days.

(21) Appl. No.: 13/469,683

(22) Filed: May 11, 2012

(65) Prior Publication Data

US 2012/0296298 A1 Nov. 22, 2012

Related U.S. Application Data

(60) Provisional application No. 61/487,413, filed on May 18, 2011.

(51) Int. Cl.
*A61F 13/53* (2006.01)
*A61L 15/60* (2006.01)
*A61L 15/42* (2006.01)
*A61L 15/48* (2006.01)

(52) U.S. Cl.
CPC ............... *A61L 15/60* (2013.01); *A61L 15/425* (2013.01); *A61L 15/48* (2013.01)
USPC .......................................... 604/372; 604/367

(58) Field of Classification Search
CPC ........ A61F 2013/530481; A61F 2013/530569; A61F 2013/530591
See application file for complete search history.

(56) References Cited

U.S. PATENT DOCUMENTS

| | | | |
|---|---|---|---|
| 5,338,766 A * | 8/1994 | Phan et al. ........................ | 521/63 |
| 5,350,799 A * | 9/1994 | Woodrum et al. ............ | 525/54.3 |
| 6,107,358 A | 8/2000 | Harada et al. | |
| 6,254,990 B1 | 7/2001 | Ishizaki et al. | |
| 7,144,474 B1 * | 12/2006 | Hansen et al. .................... | 162/12 |
| 2001/0001312 A1 | 5/2001 | Mitchell et al. | |
| 2005/0054999 A1* | 3/2005 | Morman et al. .............. | 604/367 |
| 2005/0075617 A1* | 4/2005 | Vartiainen ...................... | 604/360 |
| 2005/0142965 A1* | 6/2005 | LaFortune ........................ | 442/59 |
| 2006/0025030 A1* | 2/2006 | Funk et al. ...................... | 442/118 |
| 2008/0160856 A1* | 7/2008 | Chen et al. ...................... | 442/341 |
| 2008/0234645 A1* | 9/2008 | Dodge et al. ................... | 604/368 |
| 2010/0268181 A1* | 10/2010 | Ziemer et al. ................... | 604/369 |
| 2011/0136986 A1* | 6/2011 | Elliott et al. ................. | 525/329.8 |
| 2012/0001122 A1* | 1/2012 | Wattebled et al. ............. | 252/194 |
| 2012/0232177 A1 | 9/2012 | Lopez Villanueva et al. | |
| 2012/0296295 A1 | 11/2012 | Gray et al. | |
| 2012/0296296 A1 | 11/2012 | Di Cintio et al. | |
| 2012/0296297 A1 | 11/2012 | Di Cintio et al. | |

OTHER PUBLICATIONS

PCT International Search Report, mailed Jul. 5, 2012, 5 pages.

* cited by examiner

*Primary Examiner* — Susan Su
(74) *Attorney, Agent, or Firm* — Andres E. Velarde; Amanda T. Barry

(57) ABSTRACT

A feminine hygiene absorbent article comprising water-absorbing polymer particles, obtainable by polymerization of a foamed monomer solution or suspension, drying, grinding and classification.

13 Claims, No Drawings

FEMININE HYGIENE ABSORBENT ARTICLES COMPRISING WATER-ABSORBING POLYMER PARTICLES

CROSS REFERENCE TO RELATED APPLICATION(S)

This application claims the benefit of U.S. Provisional Application No. 61/487,413, filed May 18, 2011.

FIELD OF THE INVENTION

The present invention relates to a feminine hygiene absorbent article comprising water-absorbing polymer particles obtainable by polymerization of a foamed monomer solution or suspension, drying, grinding and classification.

BACKGROUND OF THE INVENTION

Being products which absorb aqueous solutions, water-absorbing polymers are used to produce diapers, tampons, sanitary napkins, panty liners, wound dressings and other hygiene articles, but also as water-retaining agents in market gardening.

The production of water-absorbing polymer particles is described in the monograph "Modern Superabsorbent Polymer Technology", F. L. Buchholz and A. T. Graham, Wiley-VCH, 1998, pages 71 to 103.

Water-absorbing foams based on crosslinked monomers comprising acid groups are known, for example from EP 0 858 478 B1, WO 97/31971 A1, WO 99/44648 A1 and WO 00/52087 A1. They are produced, for example, by foaming a polymerizable aqueous mixture which comprises at least 50 mol % of neutralized, ethylenically unsaturated monomers comprising acid groups, crosslinker and at least one surfactant, and then polymerizing the foamed mixture. The polymerizable mixture can be foamed by dispersing fine bubbles of a gas which is inert toward free radicals, or by dissolving such a gas under elevated pressure in the polymerizable mixture and decompressing the mixture. The foams are used, for example, in hygiene articles for acquisition, distribution and storage of body fluids.

It was an object of the present invention to provide a feminine hygiene absorbent article comprising water-absorbing polymer particles with an improved profile of properties, such as a high saline flow conductivity (SFC) and especially a high free swell rate (FSR).

SUMMARY OF THE INVENTION

The object is achieved by a feminine hygiene absorbent article comprising water-absorbing polymer particles obtainable by polymerizing a foamed aqueous monomer solution or suspension comprising
  a) at least one ethylenically unsaturated monomer which bears acid groups and has been neutralized to an extent of 25 to 95 mol %,
  b) at least one crosslinker,
  c) at least one initiator and
  d) at least one surfactant,
  e) optionally one or more ethylenically unsaturated monomers copolymerizable with the monomers mentioned under a),
  f) optionally a solubilizer and
  g) optionally thickeners, foam stabilizers, polymerization regulators, fillers, fibers and/or cell nucleators, the monomer solution or suspension being polymerized to a polymeric foam and dried, which comprises subsequently grinding and classifying the polymeric foam. The water-absorbing polymer particles are provided in an amount of 0.1 g to 20 g, or of 0.15 g to 15 g, or of 0.2 g to 10 g, or also of 0.3 g to 5 g.

DETAILED DESCRIPTION OF THE INVENTION

The term "feminine hygiene absorbent article" is used herein in a broad sense including any article able to receive and/or absorb and/or contain and/or retain body fluids/bodily exudates such as menses, vaginal secretions, and urine. Exemplary feminine hygiene absorbent articles in the context of the present invention are disposable feminine hygiene absorbent articles. The term "disposable" is used herein to describe articles, which are not intended to be laundered or otherwise restored or reused as an article (i.e. they are intended to be discarded after a single use and preferably to be recycled, composted or otherwise disposed of in an environmentally compatible manner). Typical disposable feminine hygiene absorbent articles according to the present invention are sanitary napkins, panty liners, tampons, absorbent articles for low or moderate incontinence or the like. Absorbent articles suitable for use in the present invention include any type of structures, from a single absorbent layer to more complex multi layer structures. Certain absorbent articles typically include a fluid pervious topsheet, a backsheet, which may be fluid impervious and/or may be water vapour and/or gas pervious, and an absorbent element often called "core" comprised there between.

Absorbent articles according to the present invention can typically comprise a topsheet, a backsheet and an absorbent core.

The topsheet may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be included of natural fibers (e.g., wood or cotton fibers), synthetic fibers (e.g., polymeric fibers such as polyester, polypropylene, or polyethylene fibers) or from a combination of natural and synthetic fibers. In one embodiment, the topsheet may be made of a hydrophobic material to isolate the wearer's skin from liquids which have passed through the topsheet. If the topsheet is made of a hydrophobic material, at least the upper surface of the topsheet is treated to be hydrophilic so that liquids will transfer through the topsheet more rapidly. This diminishes the likelihood that body exudates will flow off the topsheet rather than being drawn through the topsheet and being absorbed by the absorbent core. In one embodiment, the topsheet can be rendered hydrophilic by treating it with a surfactant. Suitable methods for treating the topsheet with a surfactant include spraying the topsheet material with the surfactant and immersing the material into the surfactant.

For example, the topsheet can be a nonwoven web that can provide reduced tendency for surface wetness; and consequently facilitate maintaining body fluids absorbed by the core away from the user's skin, after wetting. One suitable topsheet material can be a thermobonded carded web which is available as Code No. P-8 from Fiberweb North America, Inc. (Simpsonville, S.C., U.S.A.). Another suitable topsheet material is available as Code No. S-2355 from Havix Co., Japan. Yet another suitable topsheet material can be a thermobonded carded web which is available as Code No. Profleece Style 040018007 from Amoco Fabrics, Inc. (Gronau, Germany).

The topsheet can include an apertured formed film. Apertured formed films can be used for the topsheet because they are pervious to body exudates and yet non-absorbent and have a reduced tendency to allow liquids to pass back through and rewet the wearer's skin Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", issued to Thompson on Dec. 30, 1975; U.S. Pat. No. 4,324,246 entitled "Disposable Absorbent Article Having A Stain Resistant Topsheet", issued to Mullane, et al. on Apr. 13, 1982; U.S. Pat. No. 4,342,314 entitled "Resilient Plastic Web Exhibiting Fiber-Like Properties", issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", issued to Ahr, et al. on Jul. 31, 1984; and U.S. Pat. No. 5,006,394 "Multilayer Polymeric Film" issued to Baird on Apr. 9, 1991.

The absorbent core can be any absorbent member which is generally compressible, conformable, non-irritating to the wearer's skin, and capable of absorbing and retaining body fluids. The absorbent core may be manufactured in a wide variety of sizes and shapes (e.g., rectangular, hourglass, "T"-shaped, asymmetric, etc.) and from a wide variety of liquid-absorbent materials commonly used in disposable pull-on garments and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core may vary (e.g., the absorbent core may have varying caliper zones, a hydrophilic gradient, a superabsorbent gradient, or lower average density and lower average basis weight acquisition zones; or may include one or more layers or structures). Further, the size and absorbent capacity of the absorbent core may also be varied to accommodate wearers ranging from infants through adults. However, the total absorbent capacity of the absorbent core should be compatible with the design loading and the intended use of the absorbent article.

The absorbent core may include other optional components. One such optional component is the core wrap, i.e., a material, typically but not always a nonwoven material, which either partially or totally surrounds the core. Suitable core wrap materials include, but are not limited to, cellulose, hydrophilically modified nonwoven materials, perforated films and combinations thereof.

The backsheet can comprise a liquid impervious film. The backsheet can be impervious to liquids (e.g., body fluids) and can be typically manufactured from a thin plastic film. However, typically the backsheet can permit vapours to escape from the disposable article. In an embodiment, a microporous polyethylene film can be used for the backsheet. A suitable microporous polyethylene film is manufactured by Mitsui Toatsu Chemicals, Inc., Nagoya, Japan and marketed in the trade as PG-P.

One suitable material for the backsheet can be a liquid impervious thermoplastic film having a thickness of from about 0.012 mm (0.50 mil) to about 0.051 mm (2.0 mils), for example including polyethylene or polypropylene. Typically, the backsheet can have a basis weight of from about 5 g/m2 to about 35 g/m2. However, it should be noted that other flexible liquid impervious materials may be used as the backsheet. Herein, "flexible" refers to materials which are compliant and which will readily conform to the general shape and contours of the wearer's body.

The backsheet can be typically positioned adjacent the outer-facing surface of the absorbent core and can be joined thereto by any suitable attachment means known in the art. For example, the backsheet may be secured to the absorbent core by a uniform continuous layer of adhesive, a patterned layer of adhesive, or an array of separate lines, spirals, or spots of adhesive. Illustrative, but nonlimiting adhesives, include adhesives manufactured by H. B. Fuller Company of St. Paul, Minn., U.S.A., and marketed as HL-1358J. An example of a suitable attachment means including an open pattern network of filaments of adhesive is disclosed in U.S. Pat. No. 4,573,986 entitled "Disposable Waste-Containment Garment", which issued to Minetola et al. on Mar. 4, 1986. Another suitable attachment means including several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment means may include heat bonds, pressure bonds, ultrasonic bonds, dynamic mechanical bonds, or any other suitable attachment means or combinations of these attachment means as are known in the art.

The backsheet may be additionally secured to the topsheet by any of the above-cited attachment means.

The absorbent article may also include such other features as are known in the art including, but not limited to, re-closeable fastening system, lotion, acquisition layers, distribution layers, wetness indicators, sensors, elasticized waist bands and other similar additional elastic elements and the like, belts and the like, waist cap features, containment and aesthetic characteristics and combinations thereof.

According to the present invention, the feminine hygiene absorbent article can be a sanitary napkin, or a pantiliner, or a tampon, or an article for low or moderate adult incontinence. For example, the feminine hygiene absorbent article of the present invention can be a sanitary napkin or a pantiliner.

The feminine hygiene absorbent article of the present invention typically comprises water-absorbing polymer particles obtainable by polymerizing a foamed aqueous monomer solution or suspension comprising
  a) at least one ethylenically unsaturated monomer which bears acid groups and has been neutralized to an extent of 25 to 95 mol %,
  b) at least one crosslinker,
  c) at least one initiator and
  d) at least one surfactant,
  e) optionally one or more ethylenically unsaturated monomers copolymerizable with the monomers mentioned under a),
  f) optionally a solubilizer and
  g) optionally thickeners, foam stabilizers, polymerization regulators, fillers, fibers and/or cell nucleators,
the monomer solution or suspension being polymerized to a polymeric foam and dried, which comprises subsequently grinding and classifying the polymeric foam. The water-absorbing polymer particles are provided in an amount of 0.1 g to 20 g, or of 0.15 g to 15 g, or of 0.2 g to 10 g, or also of 0.3 g to 5 g.

The water-absorbing polymer particles obtained are typically water-insoluble.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer a) is, for example, an acrylic acid purified according to WO 2004/035514 A1 comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The amount of monomer a) is preferably 20 to 90% by weight, more preferably 30 to 85% by weight, most preferably 35 to 75% by weight, based in each case on the unneutralized monomer a) and on the monomer solution or suspension. Based on the unneutralized monomer a) means in the context of this invention that the proportion of the monomer a) before the neutralization is used for the calculation, i.e. the contribution of the neutralization is not taken into account.

The acid groups of the monomers a) have been neutralized to an extent of 25 to 95 mol %, preferably to an extent of 40 to 85 mol %, more preferably to an extent of 50 to 80 mol %, especially preferably to an extent of 55 to 75 mol %, for which the customary neutralizing agents can be used, for example alkali metal hydroxides, alkali metal oxides, alkali metal carbonates or alkali metal hydrogencarbonates, and mixtures thereof. The neutralization can, however, also be undertaken with ammonia, amines or alkanolamines, such as ethanolamine, diethanolamine or triethanolamine In a preferred embodiment of the present invention, at least 50 mol %, preferably at least 75 mol %, more preferably at least 90 mol %, most preferably at least 95 mol %, of the neutralized monomers a) have been neutralized by means of an inorganic base, preferably potassium carbonate, sodium carbonate or sodium hydroxide.

A high degree of neutralization and a high proportion of acid groups neutralized with an inorganic base reduces the flexibility of the polymeric foams obtained and eases the subsequent grinding.

The proportion of acrylic acid and/or salts thereof in the total amount of monomers a) is preferably at least 50 mol %, more preferably at least 90 mol %, most preferably at least 95 mol %.

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, preferably at least 10 ppm by weight, more preferably at least 30 ppm by weight, especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

Preferred crosslinkers b) are pentaerythrityl triallyl ether, tetraalloxyethane, methylenebismethacrylamide, 15-tuply ethoxylated trimethylolpropane triacrylate, polyethylene glycol diacrylate, trimethylolpropane triacrylate and triallylamine Very particularly preferred crosslinkers b) are the polyethoxylated and/or -propoxylated glycerols which have been esterified with acrylic acid or methacrylic acid to give di- or triacrylates, as described, for example, in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably 1 to 10% by weight, more preferably 2 to 7% by weight and most preferably 3 to 5% by weight, based in each case on the unneutralized monomer a). With rising crosslinker content, the centrifuge retention capacity (CRC) falls and the absorption under a pressure of 21.0 g/cm$^2$ (AUL 0.3 psi) passes through a maximum.

The initiators c) may be all compounds which generate free radicals under the polymerization conditions, for example thermal initiators, redox initiators, photoinitiators.

Thermal initiators are, for example, peroxides, hydroperoxides, hydrogen peroxide, persulfates and azo initiators. Suitable azo initiators are, for example, 2,2'-azobis(2-amidinopropane)dihydrochloride, 2,2'-azobis(N,N-dimethylene)isobutyramidine dihydrochloride, 2-(carbamoylazo)isobutyronitrile, 2,2'-azobis [2-(2'-imidazolin-2-yl)propane] dihydrochloride and 4,4'-azobis(4-cyanovaleric acid).

Photoinitiators are, for example, α-splitters, H-abstracting systems and azides. Suitable α-splitters or H-abstracting systems are, for example, benzophenone derivatives such as Michler's ketone, phenanthrene derivatives, fluorine derivatives, anthraquinone derivatives, thioxanthone derivatives, coumarin derivatives, benzoin ethers and derivatives thereof, azo initiators such as the abovementioned free-radical formers, substituted hexaarylbisimidazoles or acylphosphine oxides. Suitable azides are, for example, 2-(N,N-dimethylamino)ethyl 4-azidocinnamate, 2-(N,N-dimethylamino) ethyl 4-azidonaphthyl ketone, 2-(N,N-dimethylamino)ethyl 4-azidobenzoate, 5-azido-1-naphthyl 2'-(N,N-dimethylamino)ethyl sulfone, N-(4-sulfonylazidophenyl)maleimide, N-acetyl-4-sulfonylazidoaniline, 4-sulfonylazidoaniline, 4-azidoaniline, 4-azidophenacyl bromide, p-azidobenzoic acid, 2,6-bis(p-azidobenzylidene)cyclohexanone and 2,6-bis (p-azidobenzylidene)-4-methylcyclohexanone.

The initiators c) are used in customary amounts, preferably at least 0.01 mol %, more preferably at least 0.05 mol %, most preferably at least 1 mol %, and typically less than 5 mol %, preferably less than 2 mol %, based on the monomers a).

The surfactants d) are of significance for the preparation and the stabilization of the foamed monomer solution or suspension. It is possible to use anionic, cationic or nonionic surfactants or surfactant mixtures which are compatible with one another. It is possible to use low molecular weight or else polymeric surfactants, combinations of different types or else the same type of surfactants having been found to be advantageous. Usable nonionic surfactants are, for example, addition products of alkylene oxides, especially ethylene oxide, propylene oxide and/or butylene oxide, onto alcohols, amines, phenols, naphthols or carboxylic acids. The surfactants used are advantageously addition products of ethylene oxide and/or propylene oxide onto alcohols comprising at least 10 carbon atoms, where the addition products comprise 3 to 200 mol of ethylene oxide and/or propylene oxide added on per mole of alcohol. The addition products comprise the alkylene oxide units in the form of blocks or in random distribution. Examples of usable nonionic surfactants are the addition products of 7 mol of ethylene oxide onto 1 mol of tallow fat alcohol, reaction products of 9 mol of ethylene oxide with 1 mol of tallow fat alcohol, and addition products of 80 mol of ethylene oxide onto 1 mol of tallow fat alcohol. Further usable commercial nonionic surfactants consist of reaction products of oxo alcohols or Ziegler alcohols with 5 to 12 mol of ethylene oxide per mole of alcohol, especially with 7 mol of ethylene oxide. Further usable commercial nonionic surfactants are obtained by ethoxylation of castor oil. For example, 12 to 80 mol of ethylene oxide are added on per mole of castor oil. Further usable commercial products are, for example, the reaction products of 18 mol of ethylene oxide with 1 mol of tallow fat alcohol, the addition products of 10 mol of ethylene oxide onto 1 mol of a $C_{13}/C_{15}$ oxo alcohol, or the reaction products of 7 to 8 mol of ethylene oxide onto 1 mol of a $C_{13}/C_{15}$ oxo alcohol. Further suitable nonionic surfactants are phenol alkoxylates, for example p-tert-butylphenol which has been reacted with 9 mol of ethylene oxide, or methyl ethers of reaction products of 1 mol of a $C_{12}$- to $C_{18}$-alcohol and 7.5 mol of ethylene oxide.

The above-described nonionic surfactants can be converted to the corresponding sulfuric monoesters, for example, by esterification with sulfuric acid. The sulfuric monoesters are used as anionic surfactants in the form of the alkali metal or ammonium salts. Suitable anionic surfactants are, for example, alkali metal or ammonium salts of sulfuric monoesters of addition products of ethylene oxide and/or propylene oxide onto fatty alcohols, alkali metal or ammonium salts of alkylbenzenesulfonic acid or of alkylphenol ether sulfates. Products of the type mentioned are commercially available. For example, the sodium salt of a sulfuric monoester of a $C_{13}/C_{15}$ oxo alcohol reacted with 106 mol of ethylene oxide, the triethanolamine salt of dodecylbenzenesulfonic acid, the sodium salt of alkylphenol ether sulfates and the sodium salt of the sulfuric monoester of a reaction product of 106 mol of ethylene oxide with 1 mol of tallow fat alcohol are commercial usable anionic surfactants. Further suitable anionic surfactants are sulfuric monoesters of $C_{13}/C_{15}$ oxo alcohols, paraffinsulfonic acids such as $C_{15}$ alkylsulfonate, alkyl-substituted benzenesulfonic acids and alkyl-substituted naphthalenesulfonic acids such as dodecylbenzenesulfonic acid and di-n-butylnaphthalene-sulfonic acid, and also fatty alcohol phosphates such as $C_{15}/C_{18}$ fatty alcohol phosphate. The polymerizable aqueous mixture may comprise combinations of a nonionic surfactant and an anionic surfactant, or combinations of nonionic surfactants or combinations of anionic surfactants. Cationic surfactants are also suitable. Examples thereof are the dimethyl sulfate-quaternized reaction products of 6.5 mol of ethylene oxide with 1 mol of oleylamine, distearyldimethyl ammonium chloride, lauryltrimethylammonium chloride, cetylpyridinium bromide, and dimethyl sulfate-quaternized stearic acid triethanolamine ester, which is preferably used as a cationic surfactant.

The surfactant content, based on the unneutralized monomer a) is preferably 0.01 to 10% by weight, more preferably 0.1 to 5% by weight, most preferably 0.5 to 3% by weight.

Ethylenically unsaturated monomers e) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

Solubilizers f) are water-miscible organic solvents, for example dimethyl sulfoxide, dimethylformamide, N-methylpyrrolidone, monohydric alcohols, glycols, polyethylene glycols or monoethers derived therefrom, where the monoethers comprise no double bonds in the molecule. Suitable ethers are methylglycol, butylglycol, butyldiglycol, methyldiglycol, butyltriglycol, 3-ethoxy-1-propanol and glyceryl monomethyl ether.

If solubilizers f) are used, the content thereof in the monomer solution or suspension is preferably up to 50% by weight, more preferably 1 to 25% by weight, most preferably 5 to 10% by weight.

The monomer solution or suspension may comprise thickeners, foam stabilizers, fillers, fibers and/or cell nucleators g). Thickeners are used, for example, to optimize the foam structure and to improve the foam stability. This achieves the effect that the foam shrinks only slightly during the polymerization. Useful thickeners include all natural and synthetic polymers which are known for this purpose, increase the viscosity of an aqueous system significantly and do not react with the amino groups of the basic polymer. These may be water-swellable or water-soluble synthetic and natural polymers. A detailed overview of thickeners can be found, for example, in the publications by R. Y. Lochhead and W. R. Fron, Cosmetics & Toiletries, 108, 95-135 (May 1993) and M. T. Clarke, "Rheological Additives" in D. Laba (ed.) "Rheological Properties of Cosmetics and Toiletries", Cosmetic Science and Technology Series, Vol. 13, Marcel Dekker Inc., New York 1993.

Water-swellable or water-soluble synthetic polymers useful as thickeners are, for example, high molecular weight polyethylene glycols or copolymers of ethylene glycol and propylene glycol, and high molecular weight polysaccharides such as starch, guar flour, carob flour, or derivatives of natural substances, such as carboxymethylcellulose, hydroxyethylcellulose, hydroxymethylcellulose, hydroxypropylcellulose and cellulose mixed ethers. A further group of thickeners is that of water-insoluble products such as fine silica, zeolites, bentonite, cellulose powder or other fine powders of crosslinked polymers. The monomer solution or suspension may comprise the thickeners in amounts up to 30% by weight. If such thickeners are used at all, they are present in the monomer solution or suspension in amounts of 0.1 to 10% by weight, preferably 0.5 to 20% by weight.

In order to optimize the foam structure, it is optionally possible to add hydrocarbons having at least 5 carbon atoms in the molecule to the aqueous reaction mixture. Suitable hydrocarbons are, for example, pentane, cyclopentane, hexane, cyclohexane, heptane, octane, isooctane, decane and dodecane. The useful aliphatic hydrocarbons may be straight-chain, branched or cyclic and have a boiling temperature above the temperature of the aqueous mixture during the foaming. The aliphatic hydrocarbons increase the shelf life of the as yet unpolymerized foamed aqueous reaction mixture. This eases the handling of the as yet unpolymerized foams and increases process reliability. The hydrocarbons act, for example, as cell nucleators and simultaneously stabilize the foam already formed. In addition, they can bring about further foaming in the course of polymerization of the monomer solution or suspension. They may then also have the function of a blowing agent. Instead of hydrocarbons or in a mixture therewith, it is optionally also possible to use chlorinated or fluorinated hydrocarbons as a cell nucleator and/or foam stabilizer, such as dichloromethane, trichloromethane, 1,2-dichloroethane, trichlorofluoromethane or 1,1,2-trichlorotrifluoroethane. If hydrocarbons are used, they are used, for example, in amounts of 0.1 to 20% by weight, preferably 0.1 to 10% by weight, based on the monomer solution or suspension.

In order to modify the properties of the foams, it is possible to add one or more fillers, for example chalk, talc, clay, titanium dioxide, magnesium oxide, aluminum oxide, precipitated silicas in hydrophilic or hydrophobic polymorphs, dolomite and/or calcium sulfate. The fillers may be present in the monomer solution or suspension in amounts of up to 30% by weight.

The above-described aqueous monomer solutions or suspensions are first foamed. It is possible, for example, to dissolve an inert gas, such as nitrogen, carbon dioxide or air, in the aqueous monomer solution or suspension under a pressure of, for example, 2 to 400 bar, and then to decompress it to standard pressure. In the course of decompression from at least one nozzle, a free-flowing monomer foam forms. Since gas solubility increases with falling temperature, the gas saturation and the subsequent foaming should be performed at minimum temperature, though undesired precipitations should be avoided. It is also possible to foam the aqueous monomer solutions or suspensions by another method, by dispersing fine bubbles of an inert gas therein. In the laboratory, the aqueous monomer solutions or suspensions can be foamed, for example, by foaming the aqueous monomer solution or suspension in a food processor equipped with egg beaters. In addition, it is possible to foam the aqueous monomer solutions or suspensions with carbon dioxide, by adding carbonates or hydrogencarbonates for neutralization.

The foam generation is preferably performed in an inert gas atmosphere and with inert gases, for example by admixing with nitrogen or noble gases under standard pressure or elevated pressure, for example up to 25 bar, and then decompressing. The consistency of the monomer foams, the size of the gas bubbles and the distribution of the gas bubbles in the monomer foam can be varied within a wide range, for example, through the selection of the surfactants d), solubilizers f), foam stabilizers, cell nucleators, thickeners and fillers g). This allows the density, the open-cell content and the wall thickness of the monomer foam to be adjusted easily. The aqueous monomer solution or suspension is preferably foamed at temperatures which below the boiling point of the constituents thereof, for example at ambient temperature up to 100° C., preferably at 0 to 50° C., more preferably at 5 to 20° C. However, it is also possible to work at temperatures above the boiling point of the component with the lowest boiling point, by foaming the aqueous monomer solution or suspension in a vessel sealed pressure-tight. This gives monomer foams which are free-flowing and stable over a prolonged period. The density of the monomer foams is, at a temperature of 20° C., for example, 0.01 to 0.9 g/cm$^3$.

The resulting monomer foam can be polymerized on a suitable substrate. The polymerization is performed in the presence of customary free-radical-forming initiators c). The free radicals can be generated, for example, by heating (thermal polymerization) or by irradiation with light of a suitable wavelength (UV polymerization).

Polymeric foams with a layer thickness of up to about 5 millimeters are produced, for example, by heating on one side or both sides, or more particularly by irradiating the monomer foams on one side or both sides. If relatively thick polymeric foams are to be produced, for example polymeric foams with thicknesses of several centimeters, heating of the monomer foam with the aid of microwaves is particularly advantageous, because relatively homogeneous heating can be achieved in this way. With increasing layer thickness, however, the proportion of unconverted monomer a) and crosslinker b) in the resulting polymeric foam increases. The thermal polymerization is effected, for example, at temperatures of 20 to 180° C., preferably in the range from 40° C. to 160° C., especially at temperatures from 65 to 140° C. In the case of relatively thick polymeric foams, the monomer foam can be heated and/or irradiated on both sides, for example with the aid of contact heating or by irradiation or in a drying cabinet. The resulting polymeric foams are open-cell. The proportion of open cells is, for example, at least 80%, preferably above 90%. Particular preference is given to polymeric foams with an open-cell content of 100%. The proportion of open cells in the polymeric foam is determined, for example, with the aid of scanning electron microscopy.

After the polymerization of the monomer foam or during the polymerization, the polymeric foam is dried. In the course of this, water and other volatile constituents are removed. Examples of suitable drying processes are thermal convection drying such as forced air drying, thermal contact drying such as roller drying, radiative drying such as infrared drying, dielectric drying such as microwave drying, and freeze drying.

The drying temperatures are typically in the range of 50 to 250° C., preferably 100 to 220° C., more preferably 120 to 210° C., most preferably 150 to 200° C. The preferred residence time at this temperature in the dryer is preferably at least 10 minutes, more preferably at least 20 minutes, most preferably at least 30 minutes, and typically at most 60 minutes.

In order to avoid undesired decomposition and crosslinking reactions, it may be advantageous to perform the drying under reduced pressure, under a protective gas atmosphere and/or under gentle thermal conditions, under which the product temperature does not exceed 120° C., preferably 100° C. A particularly suitable drying process is (vacuum) belt drying.

After the drying step, the polymeric foam usually comprises less than 10% by weight of water. The water content of the polymeric foam can, however, be adjusted as desired by moistening with water or water vapor.

Thereafter, the dried polymeric foam is ground and classified, and can be ground typically by using one-stage or multistage roll mills, pin mills, hammer mills or vibratory mills. In a preferred embodiment of the present invention, the dried polymeric foam is first ground by means of a cutting mill and then further ground by means of a turbo mill Advantageously, a predried polymeric foam with a water content of 5 to 30% by weight, more preferably of 8 to 25% by weight, most preferably of 10 to 20% by weight, is ground and subsequently dried to the desired final water content. The grinding of a merely predried polymeric foam leads to fewer undesirably small polymer particles.

The water-absorbing polymer particles are screened off using appropriate screens to a particle size in the range from preferably 100 to 1 000 µm, more preferably 150 to 850 µm, most preferably of 150 to 600 µm.

The mean particle size of the polymer particles removed as the product fraction is preferably at least 200 µm, more preferably from 250 to 600 µm and very particularly from 300 to 500 µm.

The mean particle size of the product fraction may be determined by means of EDANA recommended test method No. WSP 220.2-05 "Particle size distribution", where the proportions by mass of the screen fractions are plotted in cumulated form and the mean particle size is determined graphically. The mean particle size here is the value of the mesh size which gives rise to a cumulative 50% by weight.

The proportion of particles with a particle size of at least 150 µm is preferably at least 90% by weight, more preferably at least 95% by weight, most preferably at least 98% by weight.

Polymer particles with too small a particle size lower the permeability (SFC). The proportion of excessively small polymer particles (undersize) should therefore be small.

Excessively small polymer particles are therefore typically removed and recycled into the process. The excessively small polymer particles can be moistened with water and/or aqueous surfactant before or during the recycling.

It is also possible to remove excessively small polymer particles in later process steps, for example after the surface postcrosslinking or another coating step. In this case, the excessively small polymer particles recycled are surface postcrosslinked or coated in another way, for example with fumed silica.

The proportion of particles having a particle size of at most 850 µm is preferably at least 90% by weight, more preferably at least 95% by weight, most preferably at least 98% by weight.

The proportion of particles having a particle size of at most 710 µm is preferably at least 90% by weight, more preferably at least 95% by weight, most preferably at least 98% by weight.

The proportion of particles having a particle size of at most 600 µm is preferably at least 90% by weight, more preferably at least 95% by weight, most preferably at least 98% by weight.

Polymer particles with too great a particle size are less mechanically stable. The proportion of excessively large polymer particles should therefore likewise be small.

Excessively large polymer particles are therefore typically removed and recycled into the grinding of the dried polymer gel.

To further improve the properties, the polymer particles can be surface postcrosslinked Suitable surface postcrosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239, 230.

Additionally described as suitable surface postcrosslinkers are cyclic carbonates in DE 40 20 780 C1, 2-oxazolidone and its derivatives, such as 2-hydroxyethyl-2-oxazolidone in DE 198 07 502 A1, bis- and poly-2-oxazolidinones in DE 198 07 992 C1, 2-oxotetrahydro-1,3-oxazine and its derivatives in DE 198 54 573 A1, N-acyl-2-oxazolidones in DE 198 54 574 A1, cyclic ureas in DE 102 04 937 A1, bicyclic amide acetals in DE 103 34 584 A1, oxetanes and cyclic ureas in EP 1 199 327 A2 and morpholine-2,3-dione and its derivatives in WO 2003/31482 A1.

Preferred surface postcrosslinkers are ethylene carbonate, ethylene glycol diglycidyl ether, reaction products of polyamides with epichlorohydrin and mixtures of propylene glycol and 1,4-butanediol.

Very particularly preferred surface postcrosslinkers are 2-hydroxyethyloxazolidin-2-one, oxazolidin-2-one and 1,3-propanediol.

In addition, it is also possible to use surface postcrosslinkers which comprise additional polymerizable ethylenically unsaturated groups, as described in DE 37 13 601 A1.

The amount of surface postcrosslinker is preferably 0.001 to 2% by weight, more preferably 0.02 to 1% by weight and most preferably 0.05 to 0.2% by weight, based in each case on the polymer particles.

In a preferred embodiment of the present invention, polyvalent cations are applied to the particle surface in addition to the surface postcrosslinkers before, during or after the surface postcrosslinking The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are chloride, bromide, sulfate, hydrogensulfate, carbonate, hydrogencarbonate, nitrate, phosphate, hydrogenphosphate, dihydrogenphosphate and carboxylate, such as acetate and lactate. Aluminum sulfate is preferred. Apart from metal salts, it is also possible to use polyamines as polyvalent cations.

The amount of polyvalent cation used is, for example, 0.001 to 1.5% by weight, preferably 0.005 to 1% by weight and more preferably 0.02 to 0.8% by weight, based in each case on the polymer particles.

The surface postcrosslinking is typically performed in such a way that a solution of the surface postcrosslinker is sprayed onto the dried polymer particles. After the spraying, the polymer particles coated with the surface postcrosslinker are dried thermally, and the surface postcrosslinking reaction can take place either before or during the drying.

The spraying of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lödige Maschinenbau GmbH; Paderborn; Germany), Vricco-Nauta continuous mixers (Hosokawa Micron BV; Doetinchem; the Netherlands), Processall Mixmill mixers (Processall Incorporated; Cincinnati; US) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The penetration depth of the surface postcrosslinker into the polymer particles can be adjusted via the content of nonaqueous solvent and total amount of solvent.

When exclusively water is used as the solvent, a surfactant is advantageously added. This improves the wetting behavior and reduces the tendency to form lumps. However, preference is given to using solvent mixtures, for example isopropanol/water, 1,3-propanediol/water and propylene glycol/water, where the mixing ratio in terms of mass is preferably from 20:80 to 40:60.

The thermal drying is preferably carried out in contact driers, more preferably paddle driers, most preferably disk driers. Suitable driers are, for example, Hosokawa Bepex® horizontal paddle driers (Hosokawa Micron GmbH; Leingarten; Germany), Hosokawa Bepex® disk driers (Hosokawa Micron GmbH; Leingarten; Germany) and Nara paddle driers (NARA Machinery Europe; Frechen; Germany). Moreover, it is also possible to use fluidized bed driers.

The drying can be effected in the mixer itself, by heating the jacket or blowing in warm air. Equally suitable is a downstream drier, for example a shelf drier, a rotary tube oven or a heatable screw. It is particularly advantageous to mix and dry in a fluidized bed drier.

Preferred drying temperatures are in the range of 100 to 250° C., preferably 120 to 220° C., more preferably 130 to 210° C. and most preferably 150 to 200° C. The preferred residence time at this temperature in the reaction mixer or drier is preferably at least 10 minutes, more preferably at least 20 minutes, most preferably at least 30 minutes, and typically at most 60 minutes.

Subsequently, the surface postcrosslinked polymer particles can be classified again, excessively small and/or excessively large polymer particles being removed and recycled into the process.

In a preferred embodiment, the surface postcrosslinking is performed as early as the stage of the polymeric foam, in which case the amounts and temperatures specified for the polymer particles apply correspondingly to the polymeric foam.

To improve the properties, the polymer particles can additionally be coated or remoisturized.

The remoisturizing is carried out preferably at 30 to 80° C., more preferably at 35 to 70° C. and most preferably at 40 to 60° C. At excessively low temperatures, the polymer particles tend to form lumps, and, at higher temperatures, water already evaporates noticeably. The amount of water used for remoisturizing is preferably from 1 to 10% by weight, more preferably from 2 to 8% by weight and most preferably from 3 to 5% by weight. The remoisturizing increases the mechanical stability and reduces the tendency to static charging.

Suitable coatings for improving the free swell rate (FSR) and the saline flow conductivity (SFC) are, for example, inorganic inert substances, such as water-insoluble metal salts, organic polymers, cationic polymers and di- or polyvalent metal cations, such as aluminum sulfate and aluminum lactate. Suitable coatings for dust binding are, for example, polyols. Suitable coatings for counteracting the undesired caking tendency of the polymer particles are, for example, fumed silica, such as Aerosil® 200, and surfactants, such as Span® 20. Suitable coatings for reducing the content of unconverted monomers (residual monomers) are, for example, reducing agents such as the salts of sulfurous acid, of hypophosphorous acid and/or of organic sulfinic acid. However, the reducing agent used is preferably a mixture of the sodium salt of 2-hydroxy-2-sulfinatoacetic acid, the disodium salt of 2-hydroxy-2-sulfonatoacetic acid and sodium hydrogensulfite. Such mixtures are available as Brüggolite® FF6 and Brüggolite® FF7 (Brüggemann Chemicals; Heilbronn; Germany).

In a preferred embodiment, the remoisturizing and/or the coating is performed as early as the stage of the polymeric foam.

The present invention further provides the water-absorbing polymer particles producible from foamed monomer solutions or suspensions by the process according to the invention.

The water-absorbing polymer particles produced by the process according to the invention have a moisture content of preferably 0 to 15% by weight, more preferably 0.2 to 10% by weight and most preferably 0.5 to 8% by weight, the water content being determined by EDANA recommended test method No. WSP 230.2-05 "Moisture content".

The water-absorbing polymer particles produced by the process according to the invention have a centrifuge retention capacity (CRC) of typically at least 10 g/g, preferably at least 15 g/g, more preferably at least 20 g/g, especially preferably at least 22 g/g, very especially preferably at least 25 g/g. The centrifuge retention capacity (CRC) of the water-absorbing polymer particles is typically less than 40 g/g. The centrifuge retention capacity (CRC) is determined by the EDANA (European Disposables and Nonwovens Association) recommended test method No. WSP 241.2-05 "Centrifuge retention capacity".

The water-absorbing polymer particles produced by the process according to the invention have an absorption under a pressure of 49.2 g/cm$^2$ (AUL0.7 psi) of typically at least 10 g/g, preferably at least 13 g/g, more preferably at least 16 g/g, especially preferably at least 18 g/g, very especially preferably at least 20 g/g. The absorption under a pressure of 49.2 g/cm$^2$ (AUL0.7 psi) of the water-absorbing polymer particles is typically less than 30 g/g. The absorption under a pressure of 49.2 g/cm$^2$ (AUL0.7 psi) is determined analogously to EDANA recommended test method No. WSP 242.2-05 "Absorption under pressure", except that a pressure of 49.2 g/cm$^2$ is established instead of a pressure of 21.0 g/cm$^2$.

The water-absorbing polymer particles produced by the process according to the invention have a saline flow conductivity (SFC) of typically at least $5\times10^{-7}$ cm$^3$s/g, preferably at least $20\times10^{-7}$ cm$^3$s/g, more preferably at least $35\times10^{-7}$ cm$^3$s/g, most preferably at least $50\times10^{-7}$ cm$^3$s/g. The saline flow conductivity (SFC) of the water-absorbing polymer particles is typically less than $200\times10^{-7}$ cm$^3$s/g.

The process according to the invention can produce water-absorbing polymer particles of high saline flow conductivity (SFC) and high free swell rate (FSR); more particularly, the free swell rate (FSR) increases with the particle size of the inventive water-absorbing polymer particles.

The present invention further provides a feminine hygiene absorbent article comprising water-absorbing polymer particles, in an amount of 0.1 g to 20 g, preferably of 0.15 g to 15 g, more preferably of 0.2 g to 10 g, most preferably of 0.3 g to 5 g, said particles obtainable by polymerizing an aqueous monomer solution or suspension comprising
  a) at least one ethylenically unsaturated monomer which bears acid groups and has been neutralized to an extent of 25 to 95 mol %,
  b) at least one crosslinker and
  c) at least one initiator,
  d) optionally a surfactant,
  e) optionally one or more ethylenically unsaturated monomers copolymerizable with the monomers mentioned under a),
  f) optionally a solubilizer and
  g) optionally thickeners, foam stabilizers, polymerization regulators, fillers, fibers and/or cell nucleators,
the monomer solution or suspension being polymerized and dried, wherein the monomer solution or suspension comprises water-absorbing polymer particles based on ground polymeric foams.

Constituents a) to g) of the monomer solution or suspension are each as defined above.

The water-absorbing polymer particles based on ground polymeric foams for use in the process according to the invention have a particle size of preferably less than 250 µm, more preferably less than 200 µm, most preferably less than 150 µm.

The proportion of the water-absorbing polymer particles based on ground polymeric foams, based on the monomer a), is preferably from 0.1 to 50% by weight, more preferably from 1 to 25% by weight, most preferably from 5 to 15% by weight.

The addition of the water-absorbing polymer particles based on ground polymeric foams leads to significantly improved product properties, more particularly to a significantly increased absorption under a pressure of 49.2 g/cm$^2$ (AUL 0.7 psi).

Suitable reactors for the polymerization are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on a belt is described, for example, in DE 38 25 366 A1 and U.S. Pat. No. 6,241,928. Polymerization in a belt reactor forms a polymer gel which has to be comminuted in a further process step, for example in an extruder or kneader. The polymer gels obtained can be dried, ground and classified as already described above. The water-absorbing polymer particles thus obtained can subsequently be surface postcrosslinked, coated and/or remoisturized as likewise already described above.

The present invention further provides water-absorbing polymer particles producible by the process according to the invention using ground polymeric foams.

The present invention further provides mixtures of water-absorbing polymer particles producible using ground polymeric foams.

To this end, the inventive water-absorbing polymer particles can be mixed with noninventive polymer gels and/or noninventive water-absorbing polymer particles. The method of mixing is not subject to any restrictions.

The proportion of the inventive water-absorbing polymer particles in the mixture is preferably from 0.1 to 90% by weight, more preferably from 1 to 50% by weight, most preferably from 5 to 25% by weight.

The inventive mixtures are notable for a surprisingly high saline flow conductivity (SFC).

According to the present invention, the feminine hygiene absorbent article can comprise the water-absorbing polymeric particles typically in the absorbent core as it is known in the art, in the selected amount as specified above. They can be for example distributed within a fibrous material, such as fluff pulp, or comprised in a layer between containing, e.g. fibrous, sheets, thus forming a laminate structure. The water-absorbing polymeric particles can be comprised in a feminine hygiene absorbent article according to the present invention in addition or as an alternative to traditional superabsorbent polymers or absorbent gelling materials.

The amount of the water-absorbing polymer particles can be evaluated, typically in a feminine hygiene absorbent product containing it, with any suitable method, such as for example by means of a superabsorbent polymer titration method, as it is known to the skilled person.

In the feminine hygiene absorbent article according to the present invention the core may be generally selected from any of the absorbent cores or core systems known in the art. As used herein the term absorbent core refers to any material or multiple material layers whose primary function is to absorb, store and distribute fluid.

For example, the absorbent core can include the following components: (a) an optional fluid distribution layer for example comprising a primary fluid distribution layer together with a secondary fluid distribution layer; (b) a fluid storage layer; (c) an optional fibrous ("dusting") layer underlying the storage layer; and (d) other optional components. According to the present invention, the water-absorbing polymer particles can be provided in at least one of said layers, for example in the fluid storage layer. For example, the water-absorbing polymer particles can be comprised in the storage layer of such a composite core construction, comprised between a fibrous primary fluid distribution layer and a fibrous dusting layer. The water-absorbing polymer particles can for example be comprised as a layer entirely constituting the storage layer in such a composite core structure, comprised between suitable fibrous layers which in turn can constitute the fluid distribution layer and the dusting layer. In all embodiments of the present invention, such as those described above, the water-absorbing polymeric foam can be typically incorporated in the selected amount specified above.

The water-absorbing polymeric foams for use in accordance with the invention have a high absorption capacity for blood and a high free swell rate, and are therefore particularly suitable for use in feminine hygiene articles for absorption of menses, vaginal secretions, as well as urine.

This is particularly desirable as traditional superabsorbent materials may in comparison have less than optimal absorption and retention capacity towards body fluids such as menses and vaginal secretions due to the viscosity and/or complex nature of these fluids. Menses and vaginal secretions are in fact water based fluids comprising components having molecular weights higher than water and also corpuscular components, including red cells, white cells, soluble proteins, cellular debris and mucus, which slow down the absorption of these fluids by superabsorbents. Menses and vaginal secretions are rather thick, and more difficult to absorb in absorbent structures with conventional absorbent gelling materials; moreover, corpuscular components like red cells may decrease the absorption capacity of certain superabsorbent particles. This translates into a slower initial uptake rate of the fluid into the superabsorbent material, and in turn in the absorbent article comprising the superabsorbent material, which can result in a lower final absorption and retention capacity.

Feminine hygiene absorbent articles of the present invention have hence an improved absorption and retention of menses, vaginal secretions or urine.

The feminine hygiene absorbent articles can for example comprise a water-impervious backside, a water-pervious topside and, in between, an absorbent core of the inventive polymer particles and cellulose fibers.

In general, the proportion of the water-absorbing polymer particles in an absorbent core such as those described above can be for example 20 to 100% by weight, more preferably 40 to 100% by weight, most preferably 60 to 100% by weight.

Methods:

The measurements should, unless stated otherwise, be carried out at an ambient temperature of $23\pm2°$ C. and a relative air humidity of $50\pm10\%$. The water-absorbing polymer particles are mixed thoroughly before the measurement.

Saline Flow Conductivity

The saline flow conductivity (SFC) of a swollen gel layer under a pressure of 63.3 g/cm² (0.9 psi) is, as described in EP 0 640 330 A1, determined as the gel layer permeability of a swollen gel layer of water-absorbing polymer particles, the apparatus described on page 19 and in FIG. 8 in the aforementioned patent application having been modified to the effect that the glass frit (40) is not used, and the plunger (39) consists of the same polymer material as the cylinder (37) and now comprises 21 bores of equal size distributed homogeneously over the entire contact area. The procedure and evaluation of the measurement remain unchanged from EP 0 640 330 A1. The flow is detected automatically.

The saline flow conductivity (SFC) is calculated as follows:

$$SFC\ [cm^3s/g]=(Fg(t=0)\times L0)/(d\times A\times WP)$$

where Fg(t=0) is the flow of NaCl solution in g/s, which is obtained using linear regression analysis of the Fg(t) data of the flow determinations by extrapolation to t=0, L0 is the thickness of the gel layer in cm, d is the density of the NaCl solution in g/cm³, A is the area of the gel layer in cm², and WP is the hydrostatic pressure over the gel layer in dyn/cm².

Swell Time (Vortex)

A 100 ml beaker is initially charged with 50 ml of a 0.9% by weight sodium chloride solution, and 2.00 g of water-absorbing polymer particles are added while stirring at 600 rpm by means of a magnetic stirrer sufficiently rapidly that a lump is avoided. The time until the vortex in the liquid which arises from the stirring has closed and a smooth surface has formed is measured in seconds.

Free Swell Rate

To determine the free swell rate (FSR), 1.00 g (=W1) of water-absorbing polymer particles are weighed into a 25 ml beaker and distributed homogeneously over the base thereof. Then 20 ml of a 0.9% by weight sodium chloride solution are metered into a second beaker and the contents of this beaker are added rapidly to the first, and a stopwatch is started. As soon as the last drop of the sodium chloride solution has been absorbed, which is evident by the disappearance of the reflection on the liquid surface, the stopwatch is stopped. The exact amount of liquid which has been poured out of the second beaker and absorbed by the water-absorbing polymer particles in the first beaker is determined accurately by reweighing the second beaker (=W2). The time required for the absorption, which was measured with the stopwatch, is designated as t. The disappearance of the last liquid drop on the surface is determined as the time t.

The free swell rate (FSR) is calculated therefrom as follows:

$$FSR\ [g/gs]=W2/(W1\times t)$$

When the moisture content of the water-absorbing polymer particles is more than 3% by weight, the weight W1 has to be corrected by this moisture content.

Free Swell Capacity

The free swell capacity (FSC) of the water-absorbing polymer particles is determined by EDANA recommend test method No. WSP 240.2-05 "Free Swell Capacity".

Centrifuge Retention Capacity

The centrifuge retention capacity (CRC) of the water-absorbing polymer particles is determined by EDANA recommended test method No. WSP 241.2-05 "Centrifuge Retention Capacity".

Absorption under a pressure of 21.0 g/cm²

The absorption under a pressure of 21.0 g/cm² (AUL0.3 psi) of the water-absorbing polymer particles is determined by EDANA recommended test method No. WSP 242.2-05 "Absorption under Pressure".

Absorption under a pressure of 49.2 g/cm²

The absorption under a pressure of 49.2 g/cm² (AUL0.7 psi) of the water-absorbing polymer particles is determined analogously to EDANA recommended test method No. WSP 242.2-05 "Absorption under Pressure", except that a pressure of 49.2 g/cm² (AUL 0.7 psi) is established instead of a pressure of 21.0 g/cm² (AUL0.3 psi).

The EDANA test methods are obtainable, for example, from EDANA, Avenue Eugene Plasky 157, B-1030 Brussels, Belgium.

EXAMPLES

The examples according to the invention describe exemplary water-absorbing polymer particles which can be comprised in feminine hygiene absorbent articles of the present invention, typically for example in the absorbent core.

Example 1

149.0 g of acrylic acid, 782.1 g of a 37.3% by weight aqueous sodium acrylate solution, 15.4 g of Sartomer® SR-344 (diacrylate of a polyethylene glycol having a molar mass of approx. 400 g/mol), 23.5 g of a 15% by weight aqueous solution of Lutensol® AT80 (addition product of 80 mol of ethylene oxide onto 1 mol of a linear saturated $C_{16}$-$C_{18}$ fatty alcohol; BASF SE; Ludwigshafen; Germany) and 30.0 g of water were mixed in a beaker.

The resulting homogeneous solution was transferred to a pressure vessel and saturated there with carbon dioxide at a pressure of 10 bar for 25 minutes. Under pressure, 14.7 g of a 3% by weight aqueous solution of 2,2'-azobis(2-amidinopropane) dihydrochloride were added and admixed with a strong carbon dioxide stream. Subsequently, carbon dioxide was passed through the reaction mixture for a further 5 minutes. The carbon dioxide-saturated reaction mixture was then extruded at a pressure of 12 bar through a die with a diameter of 1.0 mm, which formed a fine-cell, free-flowing foam.

The resulting monomer foam was applied to a glass plate of DIN A3 size with edges of height 3 mm, and covered with a second glass plate. The foam sample was irradiated with UV light synchronously from both sides over 4 minutes, from above with a UVASPOT 1000/T UV/VIS radiator (Dr. Hönle AG; Gräfelfing; Germany), and from below with 2 UVASPOT 400/T UV/VIS radiators (Dr. Hönle AG; Gräfelfing; Germany).

The resulting foam layer was completely dried in a forced air drying cabinet at 100° C., then ground in a Retsch mill and screened off to a particle size of 150 to 600 μm.
Solids content of the reaction mixture: 45.3% by weight
Degree of neutralizing: 60 mol %
Monomer foam density: 0.16 g/cm$^3$ The properties of the resulting water-absorbing polymer particles are reported in Table 1 and Table 2.

Example 2

The procedure was as in Example 1. Instead of 15.4 g of Sartomer® SR-344, only 10.3 g of Sartomer® SR-344 were used. The properties of the resulting water-absorbing polymer particles are reported in Table 1.

Example 3

The procedure was as in Example 1. Instead of 15.4 g of Sartomer® SR-344, only 7.7 g of Sartomer® SR-344 were used. The properties of the resulting water-absorbing polymer particles are reported in Table 1.

Example 4

The procedure was as in Example 1. Instead of 15.4 g of Sartomer® SR-344, only 4.4 g of Sartomer® SR-344 were used. The properties of the resulting water-absorbing polymer particles are reported in Table 1.

Example 5

The procedure was as in Example 1. Instead of 15.4 g of Sartomer® SR-344, only 2.2 g of Sartomer® SR-344 were used. The properties of the resulting water-absorbing polymer particles are reported in Table 1.

TABLE 1

Variation of the amount of crosslinker

| Ex. | Crosslinker [g] | FSC [g/g] | CRC [g/g] | Vortex [s] | SFC [$10^{-7}$ cm$^3$s/g] | AUL0.7 psi [g/g] |
|---|---|---|---|---|---|---|
| 1 | 15.4 | 33.8 | 13.1 | 8 | 85 | 20.4 |
| 2 | 10.3 | 36.9 | 16.1 | 7 | 13 | 19.1 |
| 3 | 7.7 | 38.5 | 16.9 | 6 | 8 | 17.9 |
| 4 | 4.4 | 40.1 | 18.2 | 6 | 5 | 14.5 |
| 5 | 2.2 | 43.3 | 21.1 | 6 | 0 | 10.2 |

Example 6

Noninventive

By continuously mixing deionized water, 50% by weight sodium hydroxide solution and acrylic acid, an acrylic acid/sodium acrylate solution is prepared, such that the degree of neutralization was 69 mol %. The solids content of the monomer solution was 35.5% by weight.

The polyethylenically unsaturated crosslinker used was triply ethoxylated glyceryl triacrylate (approx. 85% strength by weight). The amount used was 1.33 g per kg of monomer solution. To initiate the free-radical polymerization, per kg of monomer solution, 2.84 g of a 15% by weight aqueous sodium peroxodisulfate solution and 28.4 g of a 0.5% by weight aqueous solution of Brüggolite® FF7 (Brüggemann Chemicals; Heilbronn; Germany) were used.

The throughput of the monomer solution was 1200 kg/h. The reaction solution had a temperature of 23.5° C. at the feed.

The individual components were metered in the following amounts continuously into a List ORP 250 Contikneter reactor, (LIST AG, Arisdorf, Switzerland):
1200 kg/h of monomer solution
1.600 kg/h of triply ethoxylated glyceryl triacrylate
3.410 kg/h of sodium peroxodisulfate solution
34.10 kg/h of Brüggolite® FF7 solution Between the addition point for crosslinker and the addition sites for the initiators, the monomer solution was inertized with nitrogen.

The residence time of the reaction mixture in the reactor was 15 minutes.

The resulting product gel was applied to a belt drier. On the belt drier, an air/gas mixture flowed continuously around the polymer gel which was dried at 175° C. The residence time in the belt drier was 43 minutes.

The dried polymer gel was ground and screened off to a particle size fraction of 150 to 710 μm. The base polymer thus obtained had the following properties:
CRC: 35.7 g/g
AUL 0.3 psi: 19.1 g/g 1200 g of the base polymer were transferred to a Gebr. Lödige laboratory mixer (M5R). At approx. 23° C., a mixture of 0.6 g of 2-hydroxyethyloxazolidin-2-one, 0.6 g of 1,3-propanediol, 6.0 g of 1,2-propanediol, 22.8 g of water, 11.0 g of 2-propanol, 0.096 g of sorbitan monococoate and 5.4 g of aluminum lactate were sprayed on by means of a nozzle. The sprayed polymer particles were transferred to another Gebr. Lödige laboratory mixer, which was heated rapidly to 175° C. and held at this temperature for 50 minutes. After cooling, the surface postcrosslinked polymer particles were screened off to a screen cut between 150 and 710 μm. The properties of the resulting water-absorbing polymer particles are reported in Table 2.

Example 7

In a 500 ml glass bottle, 50 g of water-absorbing polymer particles according to Example 1 and 50 g of water-absorbing polymer particles according to Example 6 were mixed by means of a Turbula® T2F mixer (Willy A. Bachofen AG Maschinenfabrik; Muttenz; Switzerland) at 45 rpm for 15 minutes. The properties of the resulting mixture are reported in Table 2.

Example 8

In a 500 ml glass bottle, 10 g of water-absorbing polymer particles according to Example 1 and 90 g of water-absorbing polymer particles according to Example 6 were mixed by means of a Turbula® T2F mixer (Willy A. Bachofen AG Maschinenfabrik; Muttenz; Switzerland) at 45 rpm for 15 minutes. The properties of the resulting mixture are reported in Table 2.

TABLE 2

Blends with conventional water-absorbing polymer particles

| Ex. | Proportion of inventive polymer particles [% by wt.] | FSR [g/gs] | CRC [g/g] | AUL0.7 psi [g/g] | SFC [$10^{-7}$ cm$^3$s/g] |
|---|---|---|---|---|---|
| 1 | 100 | 1.70 | 13.1 | 20.4 | 85 |
| 6 | 0 | 0.18 | 29.1 | 25.2 | 129 |

TABLE 2-continued

Blends with conventional water-absorbing polymer particles

| Ex. | Proportion of inventive polymer particles [% by wt.] | FSR [g/gs] | CRC [g/g] | AUL0.7 psi [g/g] | SFC [$10^{-7}$ cm$^3$s/g] |
|---|---|---|---|---|---|
| 7 | 50 | 0.71 | 20.5 |  | 117 |
| 8 | 10 | 0.17 | 28.8 | 25.1 | 158 |

Example 9

Noninventive 17.9 g of acrylic acid and 139.6 g of a 37.3% by weight aqueous sodium acrylate solution were weighed into a 1 000 ml plastic beaker (internal diameter 105 mm and height 145 mm) While stirring by means of a magnetic crossbeam stirrer, 0.24 g of triply ethoxylated glyceryl triacrylate (approx. 85% strength by weight) and 41.0 g of water were added. Subsequently, the plastic beaker was closed with a polymer film, a PTFE-coated temperature sensor was positioned in the middle of the solution and nitrogen was passed through the solution via a glass frit.

After 30 minutes, 0.46 g of a 15% by weight aqueous solution of sodium peroxodisulfate, 0.69 g of a 0.4% by weight aqueous solution of ascorbic acid and 0.08 g of a 10% by weight aqueous solution of hydrogen peroxide were injected by means of disposable syringes, and the temperature recording was started. The maximum temperature during the polymerization was 102.5° C.

The resulting polymer gel was dried, ground and screened off to a particle size of 150 to 850 µm. The properties of the resulting water-absorbing polymer particles are reported in Table 3.

Example 10

The procedure was as in Example 9. Directly after the addition of the last initiator, 7.0 g of water-absorbing polymer particles according to Example 1 with a particle size of less than 150 µm were added. The properties of the resulting water-absorbing polymer particles are reported in Table 3.

TABLE 3

Addition of inventive polymer particles to the monomer solution

| Ex. | Addition of inventive polymer particles [g] | FSR [g/gs] | CRC [g/g] | AUL0.3 psi [g/g] |
|---|---|---|---|---|
| 9 | 0 | 0.24 | 42.8 | 8.1 |
| 10 | 7 | 0.29 | 31.2 | 17.3 |

Example 11

145.0 g of acrylic acid, 761.4 g of a 37.3% by weight aqueous sodium acrylate solution, 15.0 g of Sartomer® SR-344 (diacrylate of a polyethylene glycol having a molar mass of approx. 400 g/mol) and 34.3 g of a 10% by weight aqueous solution of Lutensol® AT80 (addition product of 80 mol of ethylene oxide onto 1 mol of a linear saturated $C_{16}$-$C_{18}$ fatty alcohol; BASF SE; Ludwigshafen; Germany) were mixed in a beaker.

The resulting homogeneous solution was transferred to a pressure vessel and saturated there with carbon dioxide at a pressure of 10 bar for 25 minutes. Under pressure, 43.5 g of a 3% by weight aqueous solution of 2,2'-azobis(2-amidinopropane)dihydrochloride were added and admixed with a strong carbon dioxide stream. Subsequently, carbon dioxide was passed through the reaction mixture for a further 5 minutes. The carbon dioxide-saturated reaction mixture was then extruded at a pressure of 12 bar through a die with a diameter of 1.0 mm, which formed a fine-cell, free-flowing foam.

The resulting monomer foam was applied to a glass plate of DIN A3 size with edges of height 3 mm, and covered with a second glass plate. The foam sample was irradiated with UV light synchronously from both sides over 4 minutes, from above with a UVASPOT 1000/T UV/VIS radiator (Dr. Hönle AG; Gräfelfing; Germany), and from below with 2 UVASPOT 400/T UV/VIS radiators (Dr. Hönle AG; Gräfelfing; Germany). The distance of the upper lamp from the monomer foam was 39 cm and the distance of the lower lamps from the monomer foam was 13 cm.

The resulting foam layer was completely dried in a forced air drying cabinet at 100° C., then ground in a Retsch mill and screened off to different particle sizes, and the free swell rate (FSR) thereof was determined
Solids content of the reaction mixture: 44.9% by weight
Degree of neutralizing: 60 mol %
Monomer foam density: 0.16 g/cm$^3$ The properties of the resulting screen cuts are reported in Table 4.

TABLE 4

Free swell rate (FSR) of individual screen cuts

| Screen cut | FSR [g/s] |
|---|---|
| <150 µm | 0.33 |
| 150 to 250 µm | 1.75 |
| 250 to 300 µm | 2.22 |
| 300 to 400 µm | 2.36 |
| 400 to 500 µm | 2.36 |
| 500 to 600 µm | 2.22 |
| 600 to 710 µm | 2.22 |
| 710 to 800 µm | 2.49 |
| 800 to 900 µm | 2.36 |
| 900 to 1000 µm | 2.45 |
| 1000 to 2000 µm | 2.35 |
| 2000 to 4000 µm | 2.10 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A feminine hygiene absorbent article comprising water-absorbing polymer particles obtainable by polymerizing a foamed aqueous monomer solution or suspension comprising
    a) at least one ethylenically unsaturated monomer which bears acid groups and has been neutralized to an extent of 25 to 95 mol%,
    b) at least one crosslinker,
    c) at least one initiator and
    d) at least one surfactant,
    the monomer solution or suspension being polymerized to a polymeric foam and dried, which comprises subsequently grinding and classifying the polymeric foam, said water-absorbing polymer particles provided in an amount of 0.1 g to 20 g;
    wherein said water-absorbing polymer particles have a saline flow conductivity of at least $5 \times 10^{-7}$ cm$^3$s/g.

2. The feminine hygiene absorbent article of claim 1, wherein at least 50 mol% of the neutralized monomers a) have been neutralized by means of an inorganic base.

3. The feminine hygiene absorbent article of claim 2, wherein the inorganic base is potassium carbonate, sodium carbonate or sodium hydroxide.

4. The feminine hygiene absorbent article of claim 1, wherein the ground polymeric foam is classified to a particle size in the range from 100 to 1 000 μm.

5. The feminine hygiene absorbent article of claim 1, wherein the monomer solution or suspension comprises at least 1% by weight of the crosslinker b), based on the unneutralized monomer a).

6. The feminine hygiene absorbent article of claim 1, wherein the monomer a) is acrylic acid to an extent of at least 50 mol%.

7. The feminine hygiene absorbent article of claim 1, wherein said water-absorbing polymer particles have a centrifuge retention capacity of at least 10 g/g.

8. A feminine hygiene absorbent article of claim 1, wherein said water-absorbing polymer particles are in a mixture with further water-absorbing polymer particles.

9. The feminine hygiene absorbent article according to claim 8, wherein the proportion of said water-absorbing polymer particles in said mixture is from 0.1 to 90% by weight.

10. The feminine hygiene absorbent article of claim 1, wherein said feminine hygiene absorbent article comprises a topsheet, a backsheet and an absorbent core comprised therebetween, wherein said absorbent core comprises said water-absorbing polymer particles.

11. The feminine hygiene absorbent article according to claim 10, wherein said feminine hygiene absorbent article is a sanitary napkin or a pantiliner.

12. A feminine hygiene absorbent article comprising water-absorbing polymer partices in an amount of 0.1 g to 20 g, said particles obtainable by polymerizing an aqueous monomer solution or suspension comprising
    a) at least one ethylenically unsaturated monomer which bears acid groups and has been neutralized to an extent of 25 to 95 mol%,
    b) at least one crosslinker,
    c) at least one initiator and
    d) at least one surfactant,
    the monomer solution or suspension being polymerized to a polymeric foam and dried, which comprises subsequently grinding and classifying the polymeric foam;
    wherein said water-absorbing polymer particles have a saline flow conductivity of typically at least $5 \times 10^{-7}$ cm$^3$s/g.

13. The feminine hygiene absorbent article according to claim 12, wherein the water-absorbing polymer particles comprised in the monomer solution or suspension have a particle size of less than 250 μm.

* * * * *